United States Patent [19]

Bowers et al.

[11] Patent Number: 4,943,586
[45] Date of Patent: Jul. 24, 1990

[54] PYRAZOLE-CONTAINING JUVENILE HORMONE MIMICS FOR PEST CONTROL, COMPOSITIONS AND USE

[75] Inventors: William S. Bowers, Tucson, Ariz.; Takeyoshi Sugiyama, Sendai, Japan

[73] Assignee: Arizona Board of Regents for the University of Arizona, Tucson, Ariz.

[21] Appl. No.: 284,394

[22] Filed: Dec. 14, 1988

[51] Int. Cl.$^5$ .................. A01N 43/56; C07D 231/12; C07D 405/06
[52] U.S. Cl. .................. 514/406; 514/404; 514/407; 548/374; 548/375; 548/376; 548/378; 548/362
[58] Field of Search ............... 548/375, 376, 378, 374, 548/362; 514/404, 406, 407

[56] References Cited

FOREIGN PATENT DOCUMENTS 3122174 12/1982 Fed. Rep. of Germany .

Primary Examiner—Robert W. Ramsuer
Attorney, Agent, or Firm—Oblon, Spivak, McClelland, Maier & Neustadt

[57] ABSTRACT

A compound having pesticidal activity and which has the following general formula:

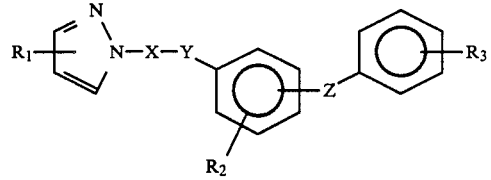

wherein:
$R_1$ is selected from hydrogen, $C_{1-6}$ alkyl, halogen, $C_{1-6}$ alkoxy, $C_{2-6}$ alkoxycarbonyl, amino, nitro, $CF_3$, and $C_{1-5}$-(alkyl and dialkyl)-amino;
X is a divalent hydrocarbon radical having 1 to 8 carbon atoms in its backbone, which may be interrupted by 1 or 2 of O or S, and which may be substituted by 1 or more halogens, $C_{1-4}$ alkyl groups or $C_{1-4}$ alkoxy groups;
Y is O, S, $CH_2$, SO, or $SO_2$;
Z is O, S, $CH_2$, SO, or $SO_2$;
$R_2$ is selected from hydrogen, halogen, $C_{1-6}$ alkyl, $C_{1-6}$ alkoxy, $C_{2-6}$ alkoxycarbonyl, amino, nitro, and $CF_3$; and
$R_3$ is selected from hydrogen, halogen, $C_{1-6}$ alkyl, $C_{1-6}$ alkoxy, $C_{2-6}$ alkoxycarbonyl, amino, nitro, $C_{1-5}$-(alkyl and dialkyl)amino, and $CF_3$.

17 Claims, No Drawings

PYRAZOLE-CONTAINING JUVENILE HORMONE MIMICS FOR PEST CONTROL, COMPOSITIONS AND USE

BACKGROUND OF THE INVENTION

1. Field of the Invention

The present invention relates to certain pyrazole-containing compounds which act as juvenile hormone mimics for pest control.

2. Description of the Background

Analogs of juvenile hormones, JH mimics, are known as candidates for pest control agents, against insects in particular. The search for such compounds with high activity, high stability, safety and ease of production has been intense. Juvenile hormone analogs have been regarded as third generation insecticides because they differ in their mode of action from other insecticides and they have low toxicity to non-target organisms. Such compounds can have an influence on every stage of insect development. For example, they can induce ovicidal effects, inhibit metamorphosis to the adult stage (death in the last larval or pupal stages), and interfere with molting of early instar larvae in certain insect species.

The first natural juvenile hormones to be identified structurally are referred to as JH 0-III. These compounds have the following structures:

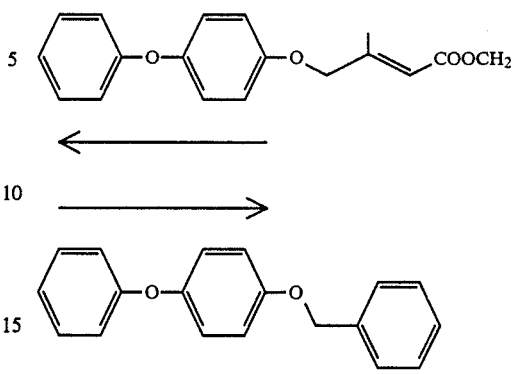

$R=R_1=R_2$=ethyl, JH 0; $R=R_1$=ethyl, $R_2$ =methyl, JH I; R=ethyl, $R_1=R_2$=methyl, JH II; $R=R_1=R_2$=methyl, JH III.

It was later found that the isoprene unit in JH I bearing the methoxy-carbonyl function can be replaced by an appropriately substituted phenoxy group with retention of juvenile hormone activity. See "Scientific Papers of the Institute of Organic and Physical Chemistry of Wroclaw Technical University," No. 22, Conference 7, pages 289–302 (1981). The replacement of the homoisoprene units by a further phenoxy group gives rise to compounds of type 1, shown below, which also show good juvenile hormone activity. Similarly, substitution of the two homoisoprene units by phenoxy groups provides compounds of type 2 having good juvenile hormone activity. It has also been found that replacement of all three isoprenoid units, the two homoisoprene units and the isoprene unit, by phenyl groups can also mimic juvenile hormone activity. Such compounds are compounds 3 shown below.

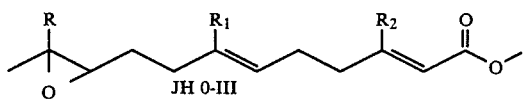

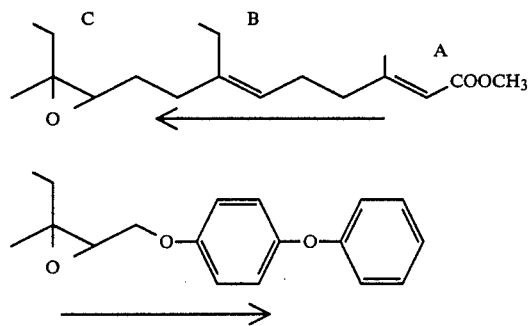

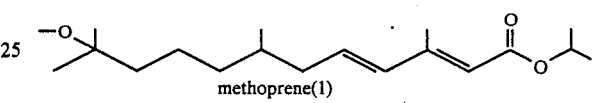

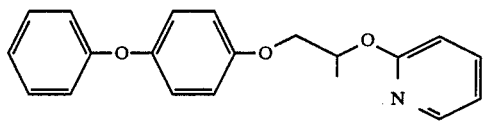

The first juvenile hormone mimic insecticide commercially produced is known as "methoprene" (1). Methoprene 1 has a terpene skeleton. Its structure is as follows:

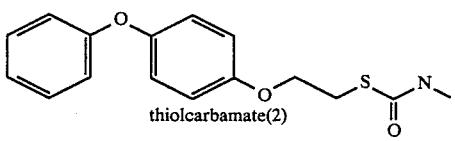

methoprene(1)

Other structures related to those shown above have been found to have juvenile hormone activity also. The compound known as Sumilarv ® having the following structure:

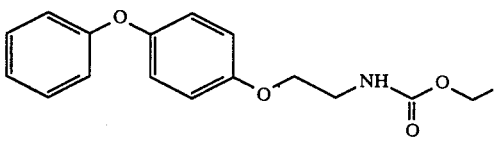

has been shown to have high juvenile hormone activity against various species of insects. It is particularly useful as a fly control agent.

The following thiolcarbamate compound has been shown to have high insect growth regulation activity:

thiolcarbamate(2)

[Recent Advances in Insect Control, 1984, pp. 103–113].

Another compound shown to have insect growth regulating properties, known as fenoxycarb ®, has the following structure:

Fenoxycarb is a non-neurotoxic insecticide which exhibits strong juvenile hormone activity against a variety of insects.

Compounds of the following structures have also been developed as potent insect juvenile hormone mimics.

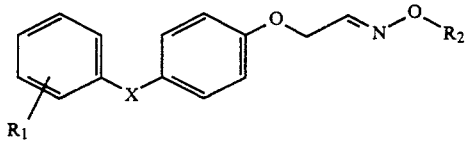

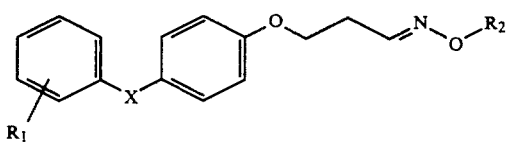

X = CH₂ or O

[J. Agric. Food Chem. 1988, 36, 378–384].

To date there have been no reports on juvenile hormone mimic compounds which contain pyrazole moieties. However, pyrazole-containing compounds have been used in the past for a variety of purposes. The following publications are exemplary.

U.S. Pat. No. 3,190,888 is directed to aryloxyalkyl-pyrazoles having pharmacological properties. In particular, the compounds are disclosed to be useful as hypoglycemic agents.

U.S. Pat. No. 4,717,734 is directed to aryl, aryloxy or arylthio(azolo-methanes) and their use as pesticides.

U.S. Pat. No. 4,151,293 is directed to insecticidal pyrazole-4-methanol esters.

DE No. 3,122,174 is directed to azoloyl-methyl ethers that have plant growth regulating and herbicidal activity.

U.S. Pat. Nos. 4,663,341, 4,689,337, 4,742,060, and Chemical Abstracts 86,12644 each disclose pyrazole-containing compounds which might be used as insecticides.

In spite of the above background, there remains a need for juvenile hormone mimic compounds which can be used to regulate insect growth.

DESCRIPTION OF THE INVENTION

It is therefore an object of the present invention to provide new compounds which have juvenile hormone mimicking activity.

It is also an object of the present invention to provide compositions containing new juvenile hormone mimic compounds.

It is yet another object to provide a method of regulating insect growth involving causing insects to come into contact with an insect growth regulating amount of a juvenile hormone mimic compound or composition.

These and other objects of the present invention as will hereinafter become more readily apparent have been achieved by the discovery that compounds of the following general structure have juvenile hormone-like activity against a variety of insects:

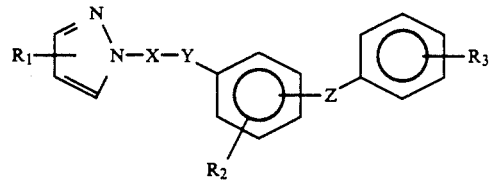

wherein:
$R_1$ is selected from hydrogen, $C_{1-6}$ alkyl, halogen, $C_{1-6}$ alkoxy, $C_{2-6}$ alkoxycarbonyl, amino, nitro, $CF_3$, and $C_{1-5}$-(alkyl and dialkyl)-amino;

X is a divalent hydrocarbon radical having 1 to 8 carbon atoms in its backbone, which may be interrupted by 1 or 2 of O or S, and which may be substituted by 1 or more halogens, $C_{1-4}$ alkyl groups or $C_{1-4}$ alkoxy groups;

Y is O, S, $CH_2$, SO, or $SO_2$;

Z is O, S, $CH_2$, SO, or $SO_2$;

$R_2$ is selected from hydrogen, halogen, $C_{1-6}$ alkyl, $C_{1-6}$ alkoxy, $C_{2-6}$ alkoxycarbonyl, amino, nitro, and $CF_3$; and $R_3$ is selected from hydrogen, halogen, $C_{1-6}$ alkyl, $C_{1-6}$ alkoxy, $C_{2-6}$ alkoxycarbonyl, amino, nitro, $C_{1-5}$-(alkyl and dialkyl)amino, and $CF_3$.

DETAILED DESCRIPTION OF THE PREFERRED EMBODIMENTS

Generally speaking, the compounds of the present invention have the following structure:

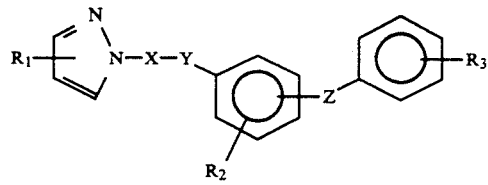

wherein:
$R_1$ is selected from hydrogen, $C_{1-6}$ alkyl, halogen, $C_{1-6}$ alkoxy, $C_{2-6}$ alkoxycarbonyl, amino, nitro, $CF_3$, and $C_{1-5}$-(alkyl and dialkyl)-amino;

X is a divalent hydrocarbon radical having 1 to 8 carbon atoms in its backbone, which may be interrupted by 1 or 2 of O or S, and which may be substituted by 1 or more halogens, $C_{1-4}$ alkyl groups or $C_{1-4}$ alkoxy groups;

Y is O, S, $CH_2$, SO, or $SO_2$;

Z is O, S, $CH_2$, SO, or $SO_2$;

$R_2$ is hydrogen, halogen, $C_{1-6}$ alkyl, $C_{1-6}$ alkoxy, $C_{2-6}$ alkoxycarbonyl, amino, nitro, and $CF_3$; and $R_3$ is selected from hydrogen, halogen, $C_{1-6}$ alkyl, $C_{1-6}$ alkoxy, $C_{2-6}$ alkoxycarbonyl, amino, nitro, $C_{1-5}$-(alkyl and dialkyl)amino, and $CF_3$.

Generally, each of the two phenyl rings and the pyrazole moiety shown in the general structure above will have at most one or two substituents other than hydrogen. When there is more than one substituent on any given ring, the substituents may be independently selected. Therefore, for example, one $R_2$ substituent may be a hydrogen, the other a halogen, and yet another an alkyl group. Generally, each ring will have at most two substituents thereon other than hydrogen. Particularly preferably each ring will have at most one substituent other than hydrogen. Most preferably, each ring will only contain hydrogen for the R groups. It is also possible for one ring to have a substituent other than hydrogen and the other rings to have no substituent other than hydrogen.

The Z substituents may be attached to the central phenyl ring ortho, meta or para with respect to the Y attachment. Preferably, the attachment will be meta or para. Particularly preferably, the attachment will be para to the Y substituent.

Salts of the present compounds are also possible. Such salts are within the scope of the present invention. Generally, such salts will be acid addition salts to a nitrogen atom. Such salts may be formed with mineral acids (e.g. HCl, HBr, $H_2SO_4$, $HNO_3$), with lower carboxylic acids (e.g. $C_{1-6}$ alkylcarboxylic acids), or with other acids which are standard in the art of insecticides or juvenile hormone mimics.

The divalent organic group for X may be any hydrocarbon organic group which may be interrupted with a small number (e.g. up to 3) of O or S atoms and which does not strongly interfere with synthesis of the molecule. The hydrocarbon group may be straight chain, branched, or may contain a cyclic structure. Preferably, the divalent group will be a straight chain molecule, and particularly preferably it will be interrupted by up to 1 O or S atom. Examples of such groups are:

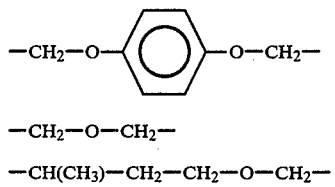

—CH₂—O—CH₂—

—CH(CH₃)—CH₂—CH₂—O—CH₂—

-continued

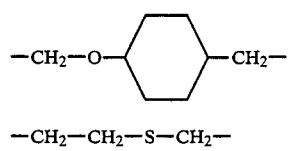

—CH₂—CH₂—S—CH₂—

X is most preferably selected from among the following groups:

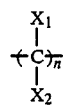

wherein n is 1–10, and

X₁ and X₂ are independently selected from hydrogen, halogen, $C_{1-4}$ alkyl, $CF_3$, OH, and $C_{1-4}$ alkoxy. Particularly preferably n is 1–8, most preferably 2 or 3. Particularly preferably X₁ and X₂ are each hydrogen.

Y is preferably oxygen.

Z is preferably oxygen.

Wherever alkyl is used herein, the alkyl group may be either straight chain, branched (for alkyl of 2 or more carbon atoms), or cyclic (for alkyl greater than two carbon atoms). Examples are methyl, ethyl, propyl, isopropyl, cyclopropyl, butyl, isobutyl, t-butyl, sec-butyl, pentyl, 3-methyl-pentyl, cyclopentyl, and cyclohexyl.

By halogen is preferably meant chlorine, bromine, fluorine or iodine, particularly preferably chlorine or fluorine.

Specific examples of preferred embodiments of the present invention are given by the following formulas:

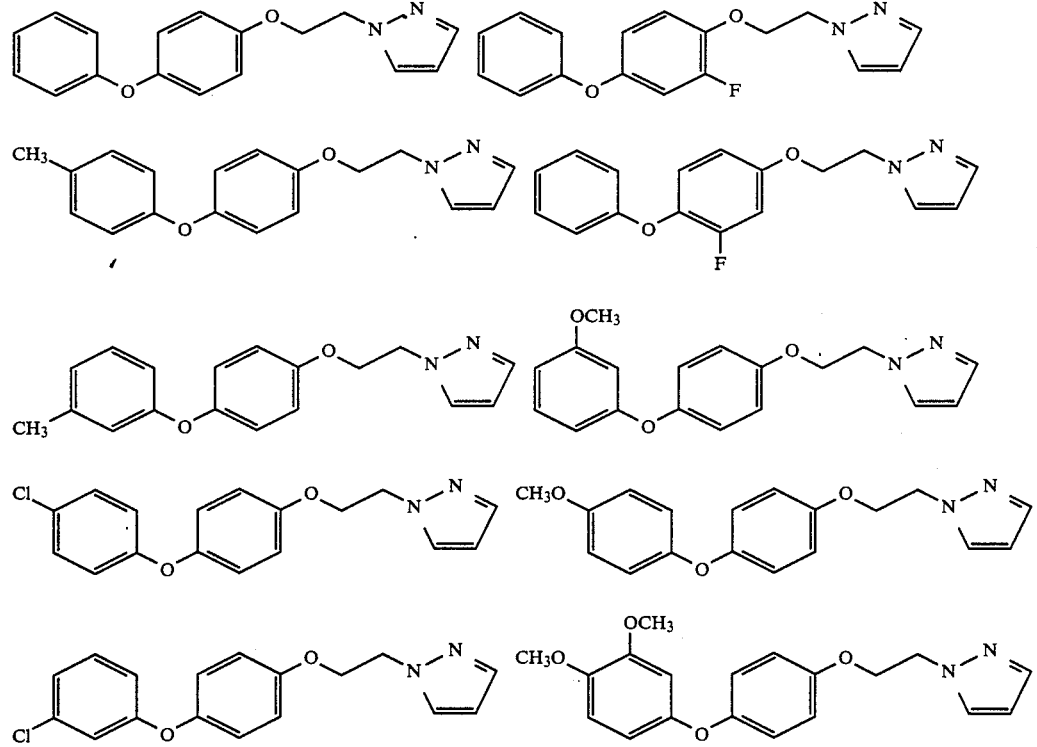

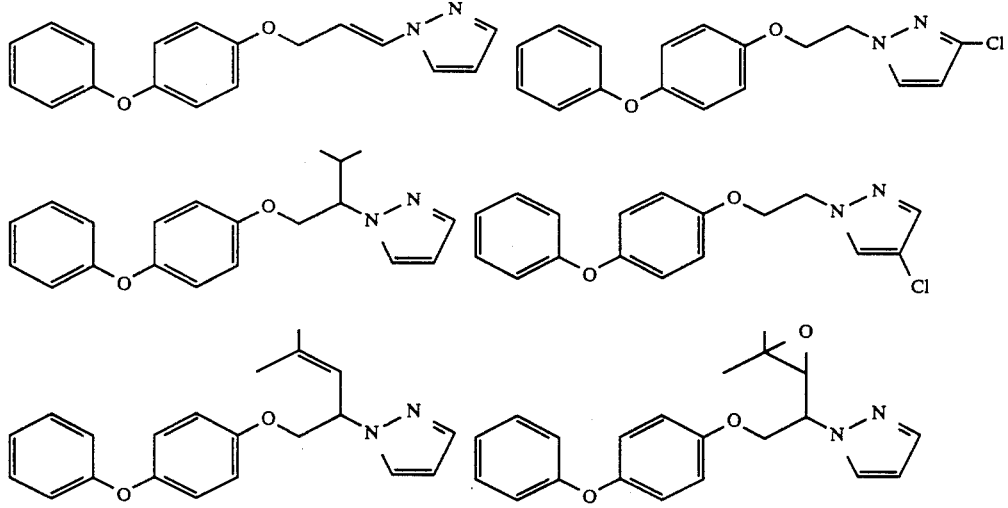

The present compounds may be synthesized by methods which are standard in the art of synthetic organic chemistry. Examples of specific and general synthetic procedures to produce compounds falling within the scope of the present invention may be found in the Examples section herein.

In general, the compounds of the present invention are expected to demonstrate a very low acute toxicity towards non-targetted organisms, such as plants, animals, and humans. The compounds are expected to be useful in treating a variety of insect species, including, but not limited to, mosquitos, flies, midges, ants, cotton leaf perforator, fleas, roaches, termites, spruce bud worm, gypsy moths, and, in general, household pests, etc. Particular species in which activity may be expected are as follows:

American cockroach, *Periplaneta americana*
German cockroach, *Blattella germanica*
Yellowfever mosquito, *Aedes aegypti*
Malaria mosquito, *Anopheles quadrimaculatus*
Northern house mosquito, *Culex pipens*
House fly, *Musca domestica*
House cricket, *Acheta domesticus*
Corn earworm, *Heliothis zea*
Differential grasshopper, *Melanoplus differentialis*
Yellow mealworm, *Tenebrio molitor.*

The compounds of the present invention may be applied directly to surfaces or on materials with which the insects are expected to come into contact, preferably during development or maturation. Thus, the compounds may be applied directly to walls, floors, external surfaces of structures, to raw garbage, in or on manure, in or on bait materials, including foods, in water, etc. Compounds or compositions may be directly applied to eggs, pupae, larvae, or adults of the insect.

The compounds may be directly applied to plants or animals. In the control of fleas, for example, the material may be applied directly, preferably in a formulation form, to the fur or hair of an animal such as a dog, cat, horse, cow, etc.

The compounds of the present invention may be administered as the compound per se, or in any other form. Preferably, the compounds are administered in combination with a carrier material or formulated into granules, flakes, etc. For particular applications, it may be desirable to avoid introduction of moisture to the site of application, and in such a case, the compounds are preferably administered in granular form. In other applications, it may be desirable to apply the present compounds by spraying in a carrier material such as an organic liquid (e.g. kerosene) or in aqueous solution or suspension. It may further be desirable to use the present compounds in combination with a bait material (e.g. granular corn grits bait for fire ants, *Salenopsis invicta* or termites). The materials may also be applied in the form of sprays including oils, powders, dusts, etc.

Particular examples of useful formulations of the present invention are as follows:

A. A wettable powder containing 0.1–25% active ingredient by weight.
B. A granular bait material containing 0.1–5% active ingredient by weight.
C. An emulsifiable concentrate containing 0.5–25 grams active ingredient per liter.
D. A dusting powder containing 0.5–20% active ingredient by weight.
E. A microemulsion containing 0.1–20% active ingredient by weight.

The compounds of the present invention may be applied as the sole active ingredient or in combination with other known insecticidal or insect growth regulating materials. For example, it may be advantageous to include an adulticide into the formulation containing the juvenile hormone mimic of the present invention to achieve more effective control of both adult and immature insects. Examples of such additional agents are as follows: pyrethrins, carbamate or organophosphorus insecticides. The proportion of such additional ingredients is not specifically limited and can readily be determined based on standard activity tests with respect to particular target pests.

The invention now being generally described, the same will become better understood by reference to the following examples which are included herein as representative of the present invention, but are not intended to be limiting thereof.

EXAMPLE OF SYNTHESIS LEADING TO ACTIVE COMPOUND #1

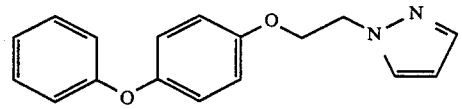

Step 1

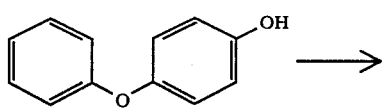

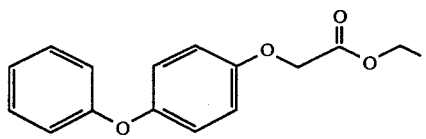

To 11.2 g, 60 mmoles, of 4-phenoxyphenol (Aldrich Chem. Co.) and 10 g (1.2 equivalents) of potassium carbonate and 10 mg of tetrabutylammonium iodide in 40 mls acetone was added 10 g, 6.67 mls, 60 mmoles (one equivalent) of ethylbromoacetate (Aldrich Chem. Co.). This was stirred and refluxed at 56° C. for 3 hours. When cooled to room temperature 2 mls (0.4 equivalents) of pyridine was added to make the water soluble pyridinium salt of any remaining ethyl bromoacetate. This was stirred at 24° C. for 15 min. and poured onto 20 mls ice water and extracted 2 times with 200 mls diethyl ether. The combined ethereal extracts were washed sequentially with 0.1N HCl, water, 1% NaOH, and brine, dried over Na₂SO₄ and evaporated to give 15.96 g of an oil, which gave a single spot on a silica thin layer chromatography plate developed with 25% ether in hexane and a single peak by capillary gas chromatography on a 12.5 m methyl silicone column, temperature programmed from 100° C. to 250° C. at 10° C. per min. Infrared and NMR spectra were consistent with the proposed structure.

Step 2

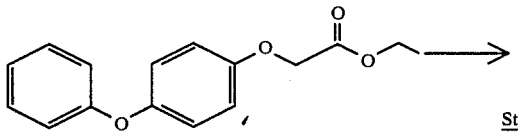

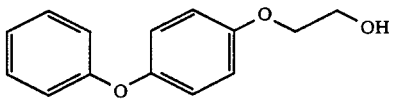

Synthesis of the alcohol: 15.90 g (58 mmoles) of the ethyl ester in 100 mls of anhydrous ethyl ether was added to 1.59 g, 42 mmoles, 0.72 molar equivalent, of lithium aluminum hydride (LAH) in 50 mls ethyl ether while maintaining the reaction below 35° C. followed by stirring at r.t. for 2 hours. Excess LAH was destroyed with ethyl acetate and then 200 mls of 0.1N HCl was added to solubilize the salts and effect an aqueous-/organic separation. The organic phase was separated and washed with brine and dried over sodium sulfate. Evaporation of the ether left 12.17 g (53 mmoles) (91% yield) of tan crystals. Thin layer chromatography on silica with 20% ethyl acetate in hexane revealed a single spot and capillary GC gave a single peak. Infrared and NMR spectra were consistent with the desired product.

Step 3

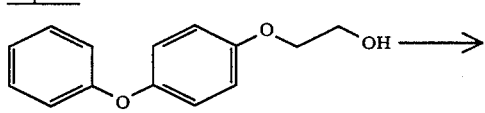

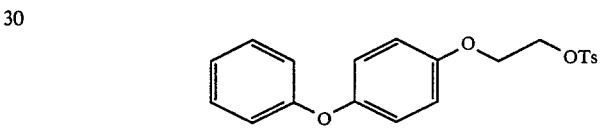

Synthesis of the tosylate. 12.0 g (50.4 mmoles) of the alcohol and 11.56 g tosyl chloride (Aldrich Chem. Co.) (1.2 equivalents) in 100 mls of pyridine was stirred at 0° C. for 4 hours. 300 mls of water were added and extracted with 200 mls of ether. The aqueous layer was re-extracted with 200 mls of ether. The combined ethereal extracts were sequentially washed with water 2×, 0.5N HCl 2×, saturated sodium bicarbonate and brine and dried over sodium sulfate. Following removal of the solvent at room temperature in vacuo the residue was crystallized from 1:1 hexane:ethyl acetate to give 16.55 g (43.1 mmoles) 85% yield of pink crystals.

Step 4

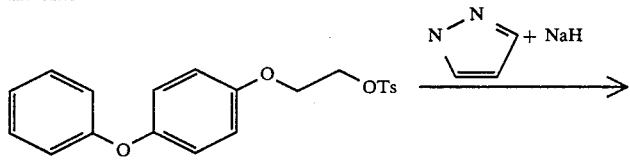

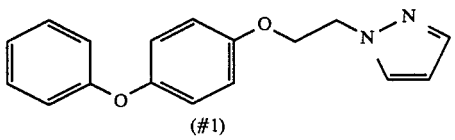

(#1)

Synthesis of the Pyrazole (Compound #1). 5.85 g (86 mmoles =2 equiv.) of pyrazole (Aldrich Chem. Co.) in 200 mls anhydrous dimethylformamide (DMF) was added dropwise to 2.17 g, 2 equiv., of sodium hydride in 20 mls dry DMF and stirred for 15 min. at 24° C. To the above 16.50 g, 43 mmoles, of the tosylate was added and stirred for 2 hours at 60° C. to 70° C. The reaction was cooled to r.t. and 550 mls water added. The reaction was extracted twice with 400 mls of diethyl ether. The ethereal extracts were combined, washed with water and brine, dried over sodium sulfate and evaporated to give 10.61 g, cloudy oil. Crystallization from 10 mls of hot 50% ethyl acetate in hexane gave a first crop of 6.67 g (23.8 mmoles, 55.3%) white crystals, and a second crop of 1.96 g yellow crystals for a total of 8.63 g (30.8 mmoles, 71.7%). Infrared, NMR and mass spectra were consistent with the expected structure.

EXAMPLES OF SYNTHESES OF RELATED COMPOUNDS

Compounds with alkyl, halogen, alkoxy, alkoxycarbonyl, amino, nitro, or $CF_3$ substitutions on the positions $R_3$ and $R_2$ could be synthesized by starting with the appropriately substituted 4-phenoxyphenol in step 1. These phenoxyphenols can be synthesized from commercially available substituted phenols with an Ullman type condensation reaction. For example: 3-Fluorobromobenzene (commercially available) can be condensed with 4-methoxyphenol, catalyzed by copper at 170° C., and then dealkylated to the phenol to give $R_3$ fluorophenoxyphenol. (Zurfluh and Dorn, 1986, abstract #2A-01, Sixth International Congress of Pesticide Chemistry, IUPAC, Ottawa.)

Similarly 4-bromo-2-fluoroanisole can be condensed with phenol to give an $R_2$ (ortho to the Y attachment) fluorophenoxyphenol.

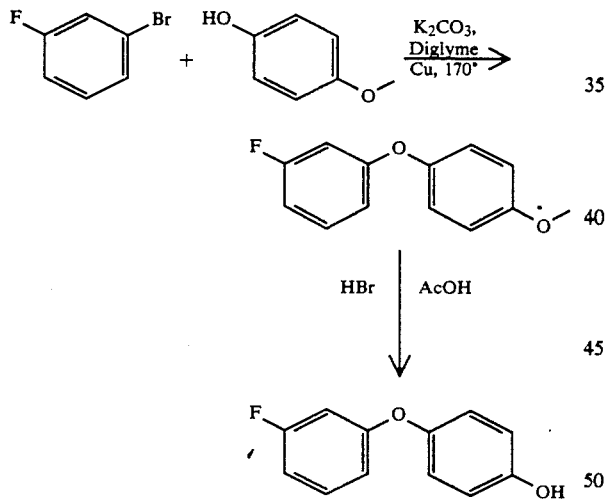

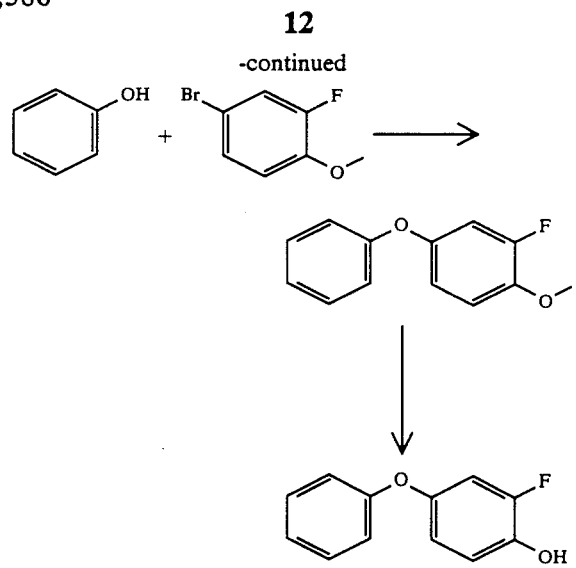

Compounds with various hydrocarbon backbones in the X position may be synthesized in several ways. For example, the reaction of molar equivalents of the phenoxyphenol with commercially available 1,4-dibromobutane and then reaction with the pyrazole as in step four would give an X of $(CH_2)_4$.

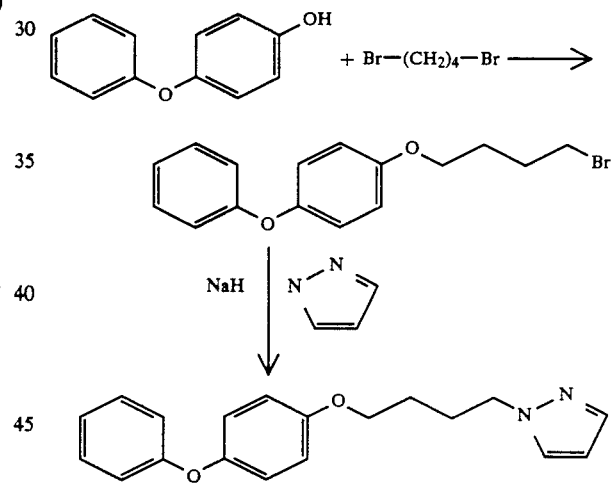

Alternatively, reaction of the phenoxyphenol with a tetrahydropryanyl protected bromo-alcohol such as a-bromo-octanol-THF followed by removal of the THP and conversion to the tosylate and reaction with a pyrazole would give an X of $(CH_2)_8$.

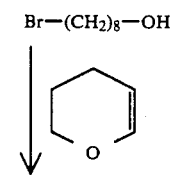

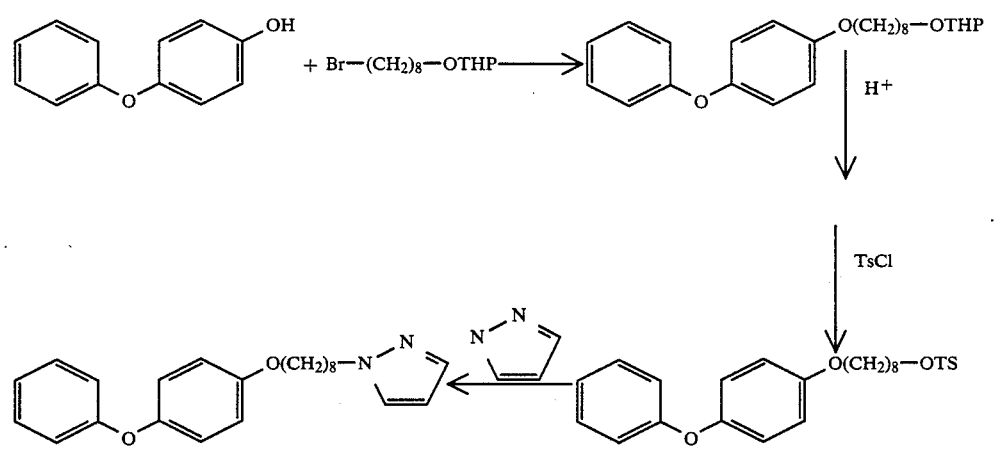

Compounds with alkyl, halogen, alkoxy, alkoxycarbonyl, amino, nitro, and CF$_3$ substituents on the pyrazole may be made by reacting the appropriately substituted commercially available pyrazoles in step 4. For example: The sodium salt of 3,5-Dimethylpyrazole is reacted with the tosylate from step 3 to give a dimethyl substituted product.

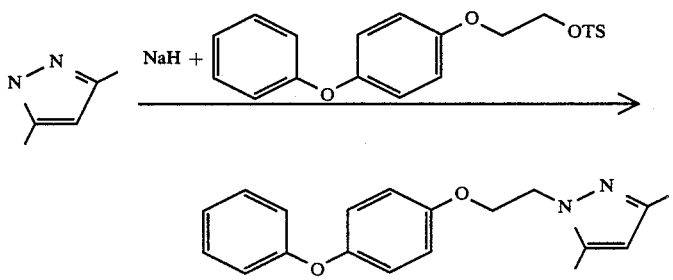

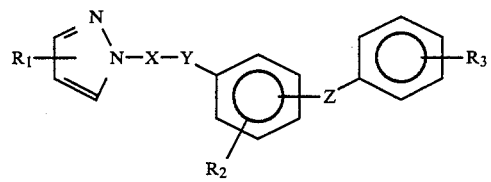

EXAMPLES OF JUVENILIZATION ACTIVITY

When early fifth instar nymphs of the large milkweed bug, *Oncopeltus fasciatus,* were treated with the pyrazole compound #1, fifty percent nymphal-adult intermediates were produced at 1.4 nanograms per insect and fifty percent perfect supernumerary insects were produced at 6.2 ng. Fifty percent of the pupae of the yellow fever mosquito *Aedes aegypti* are inhibited from eclosing to normal adults when exposed to compound #1 in the growth medium at 10 nanograms per milliliter. The pyrazole compound #1, incorporated into an artificial diet for the fruitfly *Drosophilla melanogaster* at 10 parts per million, completely inhibited adult emergence.

The invention now being fully described, it is to be understood that the invention may be practiced otherwise than as specifically described herein.

What is new and desired to be secured by letters patent of the United States is:

1. A compound having pesticidal activity and which has the following general formula:

wherein:
   R$_1$ is selected from hydrogen, C$_{1-6}$ alkyl, halogen, C$_{1-6}$ alkoxy, C$_{2-6}$ alkoxycarbonyl, amino, nitro, CF$_3$, and C$_{1-5}$-(alkyl and dialkyl)-amino;
   X is a divalent hydrocarbon radical having 1 to 8 carbon atoms in its backbone, which may be interrupted by 1 or 2 of O or S, and which may be substituted by 1 or OH groups, CF$_3$ groups halogens, C$_{1-4}$ alkyl groups or C$_{1-4}$ alkoxy groups;
   Y is O, S, SO, or SO$_2$;
   Z is O, S, SO, or SO$_2$;
   R$_2$ is selected from hydrogen, halogen, C$_{1-6}$ alkyl, C$_{1-6}$ alkoxy and C$_{2-6}$ alkoxycarbonyl; and
   R$_3$ is selected from hydrogen, halogen, C$_{1-6}$ alkyl, C$_{1-6}$ alkoxy and C$_{2-6}$ alkoxycarbonyl.

2. A compound according to claim 1, wherein R$_1$–R$_3$ are individually selected from the group consisting of hydrogen, C$_{1-6}$ alkyl, and halogen and each pyrazole or phenyl ring independently has at most 2 substituents other than hydrogen.

3. A compound according to claim 1, wherein 1 or 2 of R$_1$–R$_3$ is C$_{1-6}$ alkyl or halogen, and the rest are hydrogen.

4. A compound according to claim 1, wherein each of R$_1$–R$_3$ is hydrogen.

5. A compound according to claim 1, wherein X is

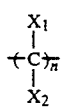

wherein n is 1–10, and

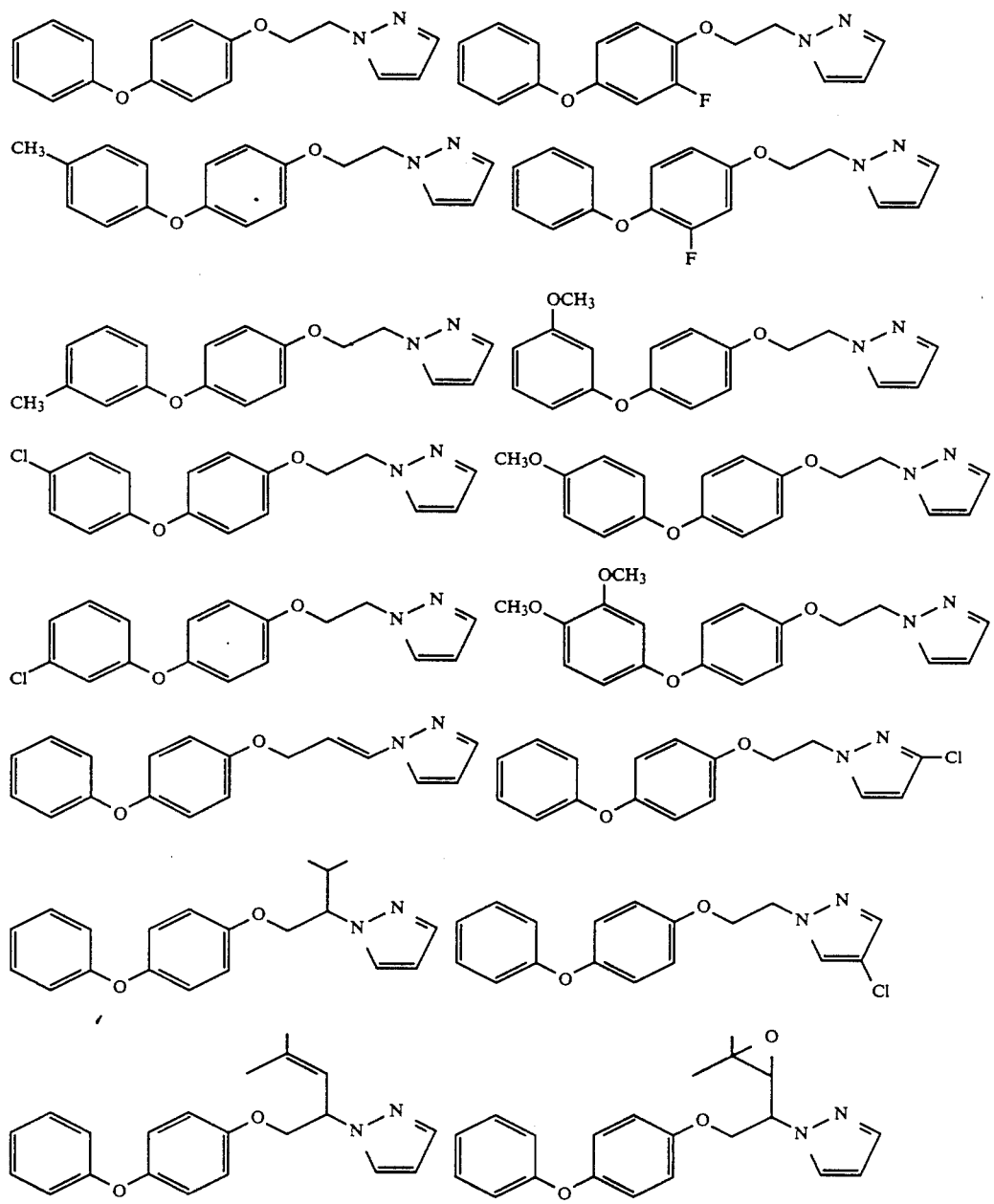

$X_1$ and $X_2$ are independently selected from halogen, $C_{1-4}$ alkyl, $CF_3$, OH, and $C_{1-4}$ alkoxy.

6. A compound according to claim 1, wherein X is

—$(CH_2)_n$—, wherein n is 1–8.

7. A compound according to claim 1, wherein Y is oxygen.

8. A compound according to claim 1, wherein Z is oxygen.

9. A compound according to claim 1, which is

10. A composition having pesticidal activity containing the compound of claim 1 in combination with a carrier material.

11. The composition according to claim 10, wherein said compound is:

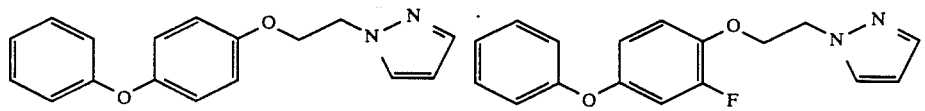

-continued

12. The composition according to claim 10, wherein said carrier material is clay.

13. The composition according to claim 10, wherein said compound is 1 to 25 wt. % relative to said carrier material.

14. The composition according to claim 10, which further comprises a second insecticidally active ingredient.

15. The composition according to claim 14, wherein said second insecticidally active ingredient is selected from pyrethroids or carbamate insecticides.

16. A method for regulating growth of insects, which comprises causing said insects to come into contact with an insect growth regulatory amount of a compound in accordance with claim 1.

17. The method of claim 16, wherein said insect is selected from the group consisting of
American cockroach, *Periplaneta americana*
German cockroach, *Blattella germanica*
Yellowfever mosquito, *Aedes aegypti*
Malaria mosquito, *Anopheles quadrimaculatus*
Northern house mosquito, *Culex pipens*
House fly, *Musca domestica*
House cricket, *Acheta domesticus*
Corn earworm, *Heliothis zea*
Differential grasshopper, *Melanoplus differentialis*, and
Yellow mealworm, *Tenebrio molitor.*

* * * * *

UNITED STATES PATENT AND TRADEMARK OFFICE
CERTIFICATE OF CORRECTION

PATENT NO. : 4,943,586

DATED : JULY 24, 1990

INVENTOR(S) : WILLIAM BOWERS ET AL.

It is certified that error appears in the above-identified patent and that said Letters Patent is hereby corrected as shown below:

Column 7, line 30, change "non-targetted" to --non-targeted--.

Column 12, line 51, change "a" to --8-- and "THF" to --THP--.

Column 14, line 50, after "or" insert --more--, and after groups (second occurrence) insert --,--.

Signed and Sealed this

Twenty-eighth Day of July, 1992

Attest:

DOUGLAS B. COMER

*Attesting Officer*     *Acting Commissioner of Patents and Trademarks*